United States Patent [19]
Kerby et al.

[11] Patent Number: 5,098,410
[45] Date of Patent: Mar. 24, 1992

[54] ADAPTER CAP ATTACHMENT

[75] Inventors: Walter L. Kerby; Rocky A. Revels, both of Sandy, Utah; Kevin P. Woehr, Münster-Amelsbüren, Fed. Rep. of Germany

[73] Assignee: Becton, Dickinson and Company, Franklin Lakes, N.J.

[21] Appl. No.: 450,093

[22] Filed: Dec. 13, 1989

[51] Int. Cl.⁵ .................... A61M 5/00; A61M 5/14
[52] U.S. Cl. ..................... 604/256; 604/280; 604/284; 604/236; 604/238; 215/306; 215/316; 220/306; 220/375
[58] Field of Search ............... 604/30, 33, 34, 36, 604/64, 164–167, 192, 197, 236, 240–242, 284, 256; 128/88; 215/316, 306; 220/306, 375

[56] References Cited
U.S. PATENT DOCUMENTS

| | | | |
|---|---|---|---|
| 3,416,567 | 2/1965 | Von Dordel et al. | 604/83 |
| 3,802,433 | 4/1974 | Raven | 604/283 |
| 4,047,648 | 9/1977 | Croyle | 220/375 |
| 4,082,201 | 4/1978 | Bitkl | 215/306 |
| 4,231,367 | 11/1980 | Rash | 604/165 |
| 4,246,932 | 1/1981 | Raines | 604/30 |
| 4,329,989 | 5/1982 | Dallons et al. | 604/192 |

*Primary Examiner*—John D. Yasko
*Assistant Examiner*—Chalin Smith
*Attorney, Agent, or Firm*—Aaron Passman; Arthur D. Dawson

[57] ABSTRACT

An infusion catheter adapter and cap assembly, the catheter adapter has a housing with an input, an output and a side port, normal to the housing axis, which has a cap. The cap is fixedly attached to the housing by a living hinge with a retaining knob. The retaining knob on the living hinge conjugates with a groove on the housing. The groove is formed as a transverse channel defined by two opposing locking fingers. The position of the retaining knob in the groove is further ensured by a recess on the knob which conjugates with a peak in the groove to center and lock the retaining knob in the groove.

6 Claims, 4 Drawing Sheets

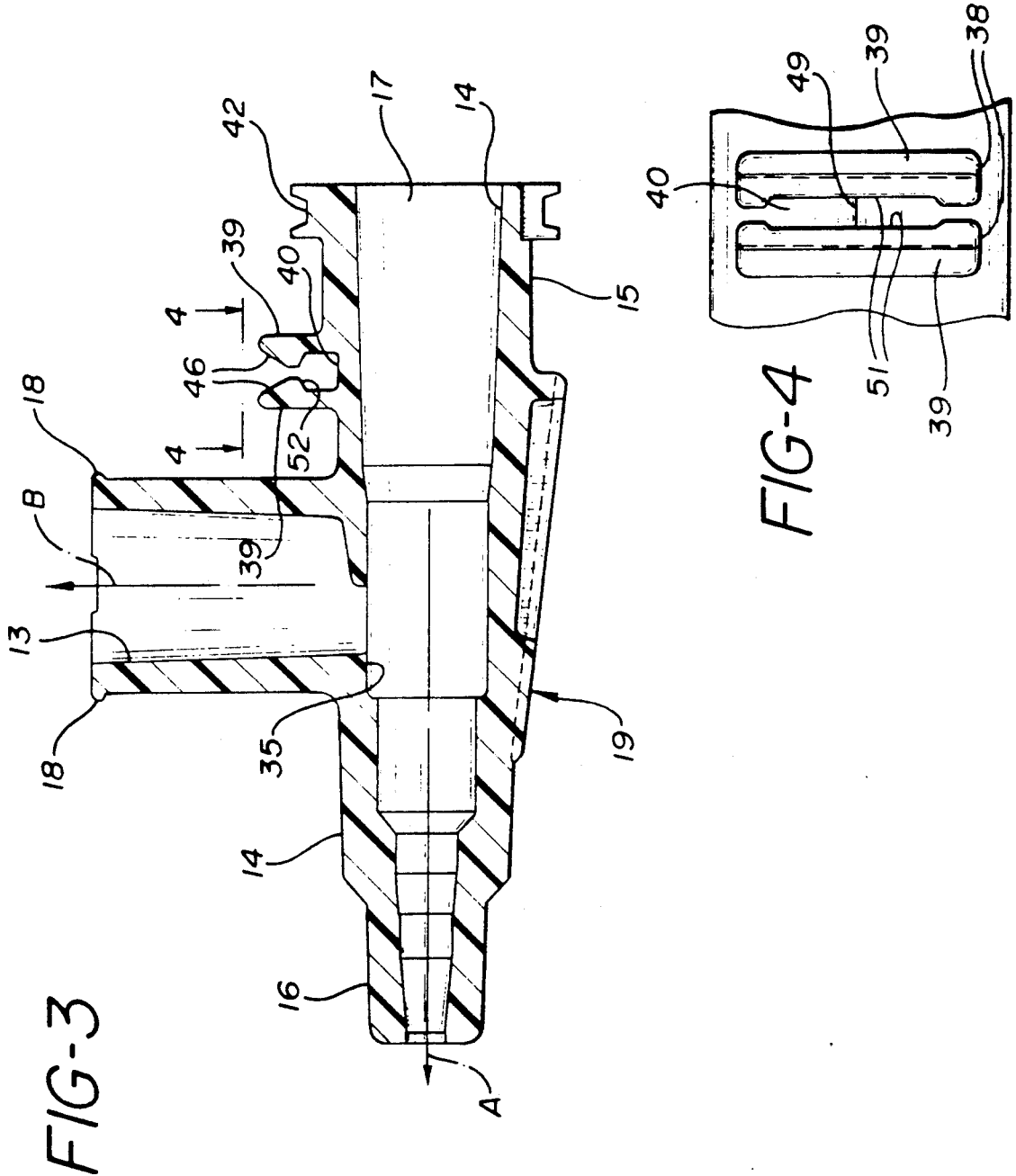

ADAPTER CAP ATTACHMENT

BACKGROUND OF THE INVENTION

1. Field of the Invention

This invention relates to an adapter and cap assembly and a method for assembling a cap to an adapter for an infusion device or the like, and more specifically, to a method of attachment and the structures for an attachment between the cap for an inlet on an adapter housing and the housing.

2. Background Description

U.S. Pat. No. 3,416,567 has an adapter of the type described herein except the cap and its living hinge assembly appear to be a part of the body of the adapter. That is to say that they appear to be molded as a single part and of the same polymer as the body of the adapter. There is no specific showing or description of the specific attachment between the living hinge of the cap and the adapter body. The body also includes a sleeve therein to close off the inlet passage so that flow into the main passage of the adapter is restricted such that outflow cannot occur.

U.S. Pat. No. 3,802,433 is an adapter wherein a catheter of thermoplastic material is mounted inside the adapter and held therein by a sleeve shaped insert. This particular patent is specifically directed to the connection between the catheter and the adapter in order to secure them together and maintain a fluid tight connection. The adapter has a cap shown in FIG. 1 attached to the socket but no specific teaching appears in the patent describing the attachment.

U.S. Pat. No. 4,063,555 shows another adapter for a catheter wherein an inlet includes a check valve in order to assure that flow into the adapter cannot be reversed. No specific cap or construction of a cap are disclosed in this patent.

U.S. Pat. No. 4,231,367 shows still another adapter wherein the cap assembly is held to the body by means of a living hinge and what would appear to be a flexible ring which surrounds the body of the inlet. There is no specific description of how this is applied and the understanding of it is primarily by means of examining FIG. 1 therein.

U.S. Design Pat. No. 256,617 shows another approach to retaining the cap wherein the living hinge and cap assembly appear to have been molded as part of the adapter body. There is no specific teaching of any other form of attachment. The need to provide a securely assembled cap and adapter which allows the cap to be of a relatively flexible material and the adapter of a material less flexible than the cap is missing in the prior references.

SUMMARY OF THE INVENTION

In the preferred form of the invention an adapter and cap assembly include a housing with a input and an output. The housing has a passage aligned along an axis thereof which passage passes from the input to the output. A generally cylindrical inlet extends from the housing in a first direction normal to the axis and the inlet intersects with the housing permitting fluid communication between the inlet and the axial passage. A mouth in the inlet is shaped for connecting in fluid tight manner with an infusion device and the mouth has lips extending radially therefrom.

Another part of the preferred assembly is a cap having a generally cylindrical side wall with an inner surface configured to conjugate with and close the inlet when placed thereover and to open the mouth when the cap is removed therefrom. An undercut in the inner side wall of the cap conjugates and releasably locks to the lips. A protrusion extends from the side wall one way and a living hinge terminating in a knob extends the other way. The protrusion may be used to remove the cap from the inlet when the undercut thereon is engaged with the lips.

A pair of opposed locking fingers most preferably extends from the housing and defines a groove therebetween. The locking fingers are shaped for receiving and securing therebetween the knob in the groove as the knob may have a camming nose with opposed tapers which cooperate with a ramp on each of the pair of locking fingers to spread the fingers as the knob is inserted therebetween and to ease the seating of the knob in the groove. The knob might include a distal end with a furrow located transverse thereto and the groove has preferably a peak transversely centered therein so that the central position of the knob in the groove is maintained upon engagement. The knob is most preferably transversely thicker than the living hinge and the knob extends normal thereto with a shoulder thereabout. Each ramp has an opposed central recess for cooperating as the camming nose is forced thereover and between so that the conjugating motion of the knob and the pair of locking fingers spreads the locking fingers apart until the peak and furrow are fully together. On each locking finger a land may be positioned normal to the inward taper of the ramp of each and is located above the groove for engagement with the shoulder on the knob.

The preferred invention may also be a method of assembly for an adapter and an inlet cap with the step of holding the living hinge on the housing in position relative to the inlet for allowing the cap to be placed on or removed from the inlet. An additional step in the assembly of locating on the knob a camming nose with opposed tapers which nose cooperates with a ramp on each of the pair of locking fingers may be included. The preferred method of assembly may also have the step of spreading the fingers by inserting the camming nose between the ramps to move the locking fingers apart when seating the knob in the groove as the knob is pressed toward the housing in the direction normal to the axis. To exactly position the knob in the groove the final step of centering the knob in the groove with a furrow located transversely across a distal end of the knob and with a peak centered in and transversely across the groove will follows conjugating a shoulder formed at the transversely thicker portion of the knob where it joins the living hinge with a land on each locking finger, each land is positioned normal to the inward taper of the ramp of each and located above the groove.

BRIEF DESCRIPTION OF THE DRAWINGS

FIG. 3 is an enlarged cross sectional view, taken along line 3—3 of FIG. 1, of the adapter of the present invention without catheter tubing, internal sleeve or cap.

FIG. 4 is an enlarged top plan view of the locking fingers of the present invention taken along lines 4—4 of FIG. 3 in order to show the details of the locking fingers for centering the knob received therebetween.

DETAILED DESCRIPTION OF THE DRAWING

Figure 1:
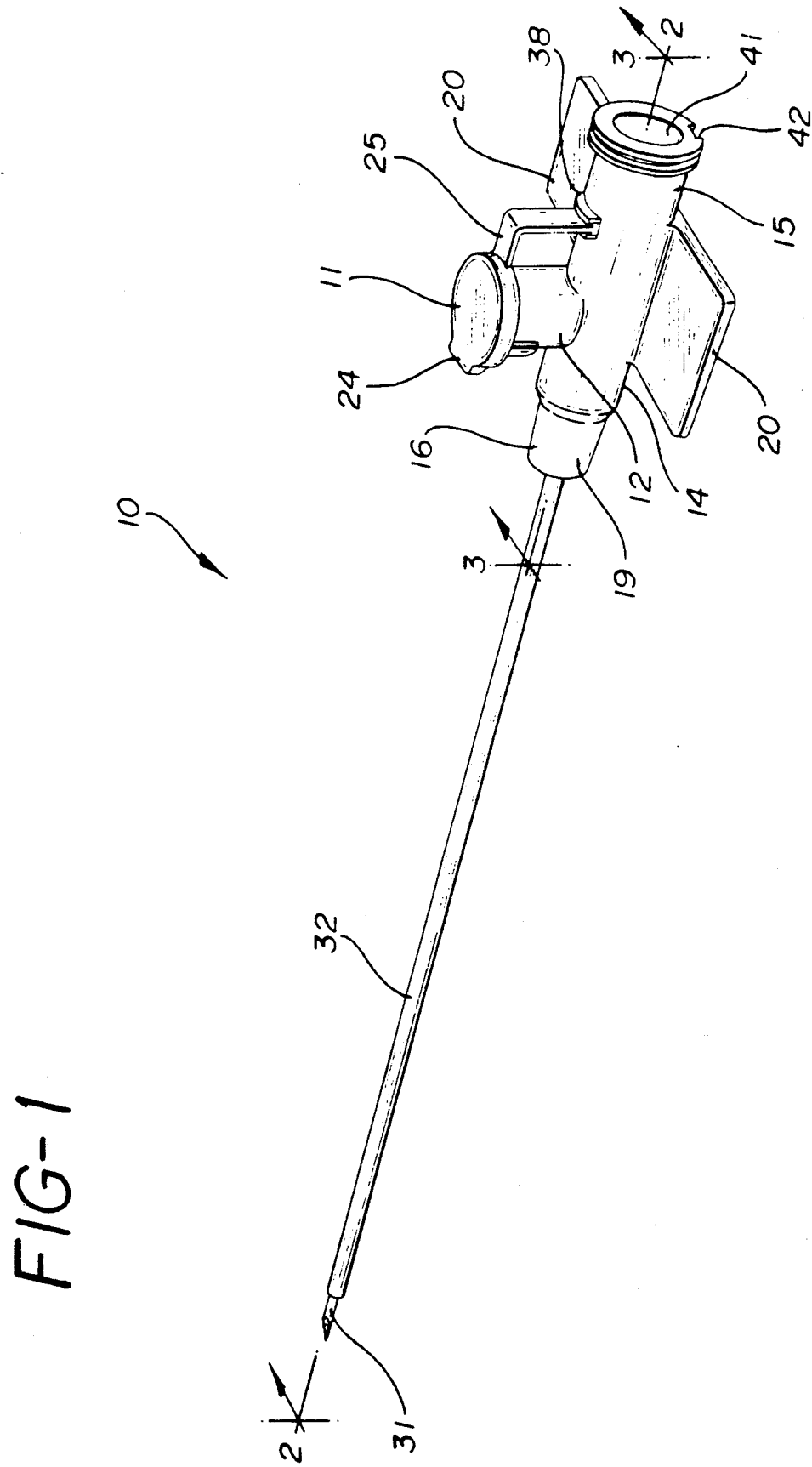
FIG. 1 is a perspective view of the preferred embodiment of an adapter and cap assembly showing the cap placed over the inlet to close the mouth thereof.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

FIG. 1 is a perspective view of the preferred embodiment of an adapter and cap assembly 10 showing a cap 11 placed over an inlet 12 thereto to close a mouth 13 thereof. In the preferred form of the invention the adapter and cap assembly 10 include a housing 14 with a input 15 and an output 16. The housing 14 has a passage 17 aligned along an axis A thereof which passage 17 passes from the input 15 to the output 16. The generally cylindrical inlet 12 extends from the housing 14 in a first direction indicated in FIG. 2 by an arrow B normal relative to the axis A and the inlet 12 intersects with the housing 14 permitting fluid communication between the inlet 12 and the passage 17. The mouth 13 of the inlet 12 is shaped for connecting in a fluid tight manner with an infusion apparatus not shown but by way of example and not limited to a syringe having a conical shaped tapered luer end. The mouth 13 has lips 18 extending radially therefrom for engaging the cap 11 and holding the cap 11 over the inlet 12 as a closure. The adapter 19 is shown with wings 20 in the preferred embodiment of FIG. 1 but that is not essential to the adapter and cap assembly 10.

Figure 2:
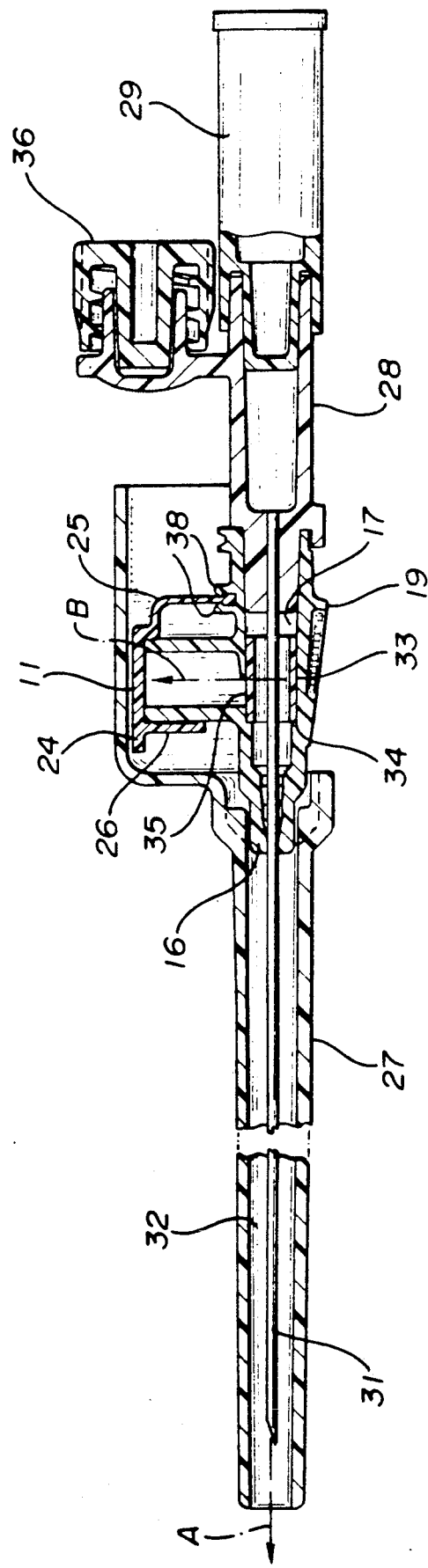
FIG. 2 is a side sectional view of the preferred embodiment of an adapter and cap assembly of FIG. 1 with the addition of the needle guard and the needle hub as well as the proximal fittings for the adapter and hub.

Another part of the preferred adapter and cap assembly 10 is the cap 11 having a generally cylindrical side wall 21 with an inner side wall surface 22 configured to conjugate with for closing the inlet 12 when placed thereover and to open the mouth 13 when the cap 11 is removed therefrom. An undercut 23 in the inner side wall surface 22 of the cap 11 conjugates with and releasably locks to the lips 18. As shown in FIGS. 1 and 2, a protrusion 24 extends from the side wall 21 one way and a living hinge 25. The protrusion 24 may be used to remove the cap 11 from the inlet 12 when the undercut 23 thereon is engaged with the lips 18. In particular, a finger placed under the protrusion 24 can easily push the cap 11 accurately upwardly for removal from the mouth 13. The side wall 21 has a greater depth or length in the direction of arrow B in the area of the protrusion 24 so that when the cap 11 is removed by pushing the protrusion 24, the medic's finger is kept away from the inlet 12. In particular, a longer part 26 of the side wall 21 is provided below the protrusion 24.

FIG. 2 is a side elevational view of the preferred embodiment of the adapter and cap assembly 10 of FIG. 1 shown in cross section with the addition of a needle guard 27 and a needle hub 28 as well as proximal fittings 29 for the adapter and the needle hub 28. The detail in FIG. 2 illustrates a complete device 30 including the adapter and cap assembly 10 as it would be available to an end user such as a doctor or nurse. The device 30 has a needle guard 27 which is preferably an elongate plastic part molded of generally transparent material thereby permitting the safe inspection of a needle 31 and catheter 32 placed coaxially thereover before insertion of the catheter 32 into a vessel during placement. The needle 31 guard 27 also covers and protects the cap 11 so that it can not be removed while the needle guard 27 is in place over the adapter 19.

The needle hub 28 extends proximally from the needle 31 and is shaped to close the input 15 of the adapter 19. The needle 31 is hollow and pointed distally to ease penetration through the skin and into the vessel. The housing 14 includes a female luer taper located on the input 15 of the housing 14 about the passage 17 and tapering outwardly of the axis along the direction of axis A from the output 16 to provide a place to connect the needle hub 28. The passage 17 near the output 16 is shaped to receive and hold a catheter 32 for fluid tight communication between the catheter 32 and the passage 17.

In use the input 15 or inlet 12 may be used to administer fluids through the inserted catheter 32 but only the input 15 can be used to extract bodily fluids. Specifically, the adapter housing 14 carries a resilient sleeve 33 inside in abutment with an annular ridge and is coaxially located inside the passage 17. The sleeve 33 is positioned relative to the axis A between the input 15 and output 16. The adapter housing 14 the passage 17 has the annular ridge 34 therein axially positioned between whose the output 16 provides the fluid tight communication with the catheter 22 and an opening or intersection 35 of the inlet 12 into the passage 17. The resilient sleeve 33 is inserted within the passage 17 abutted against the annular ridge 34 for sealing the intersection 35. The resilient sleeve 33 has an outer diameter larger than the inside of the housing 14 wherein the intersection 35 is axially located within the housing 14. The resilient sleeve 33 is thus ideal for closing the inlet 12 at the intersection 35. Pressure applied transversely to the sleeve 33 at the intersection 35 will collapse the sleeve 33 in the radial direction as per arrow B allowing flow from the inlet 12, through the intersection 35, into the passage 17 and out the output 16.

The needle hub 28 carries proximally thereon the fittings 29; the one 36 for closing the adapter input 15 is located piggy back on the needle hub 28 and the other 37 is coaxially conjugated proximally into the needle hub 28 to prevent spillage of blood flashback. FIG. 3 is an enlarged cross sectional view, taken along line 3—3 of FIG. 1, of the housing 14 of the adapter and cap assembly 10. The catheter 32, internal sleeve 33 and cap 11 are not shown in FIG. 3 so that the housing 14 as molded from for example polyproplene is apparent.

A pair 38 of opposed locking fingers 39 most preferably extends from the housing 14 in the direction indicated by arrow B and the pair 38 defines a groove 40 therebetween. The locking fingers 39 are substantially adjacent to the part of the housing 14 where the input 15 receives the needle hub 28 and has an enlarged internal diameter 41. The locking fingers 39 extend away from the housing 14 in the general direction of arrow B or parallel to the inlet 12. A luer thread 42 is about the input 15 to provide for locking an infusion apparatus having a mating thread (not shown) to the housing 14 and the pair 38 of locking fingers 39 of the preferred adapter 19 extend from the housing 14 somewhere between the luer thread 42 and the inlet 12.

Figure 5:
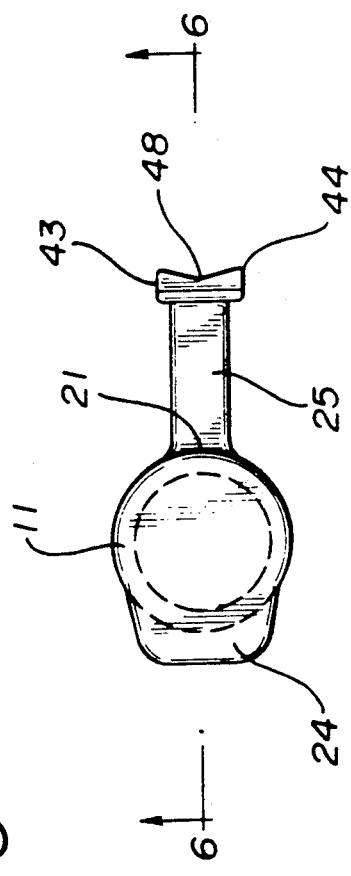
FIG. 5 is a top plan view illustrating the cap removed from the adapter and cap assembly of FIG. 1.
Figure 6:
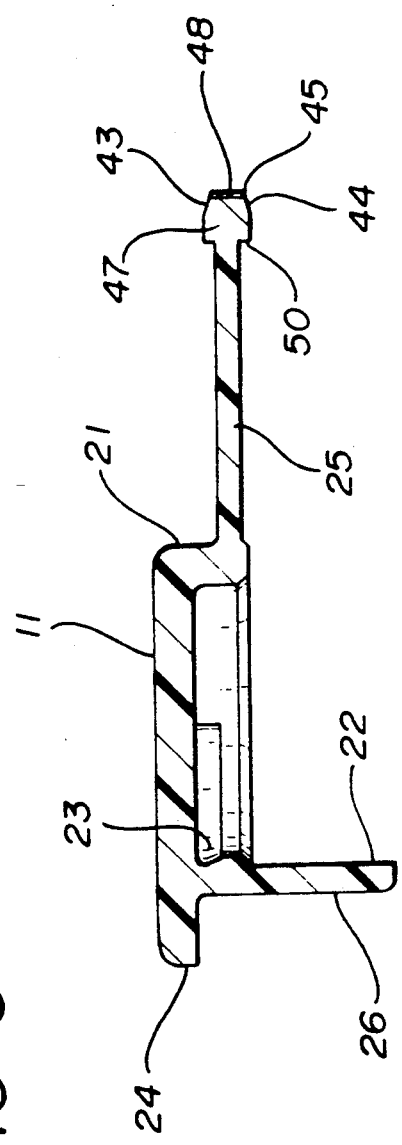
FIG. 6 is an enlarged cross sectional view taken along lines 6—6 of FIG. 5 in order to show the details of the cap.

In FIGS. 3 and 4 the details and features of the locking fingers 39 and in FIGS. 5 and 6 the living hinge 25 which terminates in an enlarged knob 43 are shown. The living hinge 25 extends, in the preferred embodiment, in the direction exactly opposite the protrusion 24 permitting the handling of the cap 11 during removal from the inlet 12 as explained. In particular in FIG. 4 there is an enlarged partial top plan view of the locking fingers 39 of the present invention as the pair 38 would appear if viewed along lines 4—4 of FIG. 3. The details of the locking fingers 39 that are useful for centering the knob 43 received therebetween are best illustrated in FIG. 4. The locking fingers 39 are shaped for receiving and securing therebetween the knob 43 in the groove 40 by sliding mating engagement. More particularly but not by way of limitation the knob 43 is an easy press fit into the groove 40 but as will be explained in greater detail in connection with the features on the knob 43 and the locking fingers 39 which cooperate to make removal rather difficult.

FIG. 5 is a top plan view illustrating the cap 11 removed from the housing 14. FIG. 6 is an enlarged cross sectional view as it would appear if examined along lines 6—6 of FIG. 5. The preferred knob 43 shown in FIGS. 5 and 6 has a camming nose 44 with opposed tapers 45 which cooperate with a ramp 46 on each of the pair 38 of locking fingers 39 to spread the fingers 39 apart in a direction generally normal to that of arrow B as the knob 43 is inserted therebetween and to ease the seating of the knob 43 in the groove 40. The knob 43 might include a distal end 47 with a furrow 48 located transverse thereto and the groove 40 has preferably a peak 49 transversely centered therein so that the central position of the knob 43 in the groove 40 is maintained upon engagement. The knob 43 is as mentioned enlarged and most preferably is transversely thicker than its living hinge 25. The knob 43 extends normal to the living hinge 25 with shoulder 50 thereabout and therebetween as a transition between the thinner and more flexible living hinge 25 and the enlarged and less flexible knob 43.

In FIG. 3 each ramp 46 has one of a pair 38 of mirror image opposed central recesses 51 positioned for cooperating as the camming nose 44 is forced and slid therebetween and thereacross so that the conjugating motion of the knob 43 and the pair 38 of locking fingers 39 spreads the locking fingers 39 apart until the peak 49 and furrow 48 are fully together. It should now be understood that the peak 49 and furrow 48 center and hold the knob 43 and groove 40 while the central recesses 51 are as will be fully explained shaped and positioned to engage and hold centered the living hinge 25 most adjacent the shoulder 50 of the knob 43. On each locking finger 39 a land 52 is positioned and forms a plane generally normal to the inward taper of the ramp 46 of each and/or the direction of arrow B. The lands 52 are located above the groove 40 for engagement with the shoulder 50 on the knob 43 such that the locking engagement of the knob 43 in the groove 40 will place the lands 52 abutted against the shoulder 50 forming a one way snap connection which can not be pulled in the direction of arrow B without first prying the locking fingers 39 apart. The complete engagement also secures the knob 43 and hinge 25 from transverse, side to side or off center movement because the locking fingers 39 come together after assembly placing the central recesses 51 about and around the living hinge 25.

The preferred invention also includes a method of assembly for the adapter 19 and the inlet 12 cap 11 by holding the living hinge 25 attached to the housing 14 in position relative to the inlet 12 for allowing the cap 11 to be easily placed on or removed from the inlet 12. An additional step in making the adapter and cap assembly 10 includes locating on the knob 43 the camming nose 44 with opposed tapers 45 which nose 44 cooperates with ramp 46 on each of the pair 38 of locking fingers 39. The preferred method of assembly may also have the step of spreading the fingers apart by inserting the camming nose 44 between the ramps 46 to move the locking fingers 39 during the process of seating the knob 43 in the groove 40 as the knob 43 is pressed toward the housing 14 in the direction of arrow B which is generally normal to the axis.

The penultimate step of the preferred method of assembly of the adapter and cap 11 requires conjugating the shoulder 50 formed at the transversely thicker portion of the knob 43 where it joins the living hinge 25 with lands 52 on each locking finger. As explained each land 52 is positioned generally normal to the inward taper of the ramp 46 of each locking figure and is located above the groove 40. To exactly position the knob 43 in the groove 40 a final step of centering the knob 43 in the groove 40 with the engagement of the furrow 48 located transversely across a distal end 47 of the knob 43 and with the peak 49 centered in and transversely across the groove 40. The knob 43 can also be assembled into the groove 40 by sliding the knob 43 sideways or transversely into the groove 40 so that it is centered therein with peak 49 and furrow 48 engaged.

Those skilled in the art will appreciate that the dimensions, application and details of the construction may be altered or reversed. For example the locking fingers 39 can be on the cap 11 and the knob 43 on the housing 14 without significantly changing the invention of the adapter and cap assembly 10. Similarly, changes in the materials described, the method of assembly and particular configuration of the adapter and cap assembly 10 disclosed may be made without departing from the scope of the invention covered by the claims which follow.

What is claimed is:
1. An adapter and cap assembly comprising:
a housing with an input and an output, the housing having a passage aligned along an axis thereof and passing through the housing from the input to the output, the housing having an inlet extending from the housing in a first direction and located generally normal to the axis and between the input and output, the inlet having an intersection with the housing for permitting fluid communication with the passage;
a cap having a side wall with an inner surface configured to conjugate with and closed the inlet when placed thereover, the cap including a living hinge extending from the side wall and terminating in a knob;
a pair of opposed generally parallel locking fingers extending from the housing to provide a groove therebetween, the locking fingers shaped for receiving and securing therebetween in the groove the knob and thereby hold the living hinge for allowing the cap to be placed on or removed from the inlet;

the knob having a camming nose with opposed tapers which cooperate with a ramp on each of the pair of locking fingers to spread the locking fingers as the knob is inserted therebetween and to thereby ease the seating of the knob in the groove; and the knob having a distal end with a furrow transversely thereacross and the groove having a peak centered therein and transverse thereto so that a central position of the knob is maintained during engagement in the groove.

2. The adapter of claim 1 wherein the knob is transversely larger than the living hinge and the knob extends normal thereto with a shoulder thereabout.

3. The adapter of claim 2 wherein the ramps on the locking fingers each have a central recess located opposite to one another to cooperate as the camming nose is forced thereacross and therebetween so that the conjugating motion of the knob and the pair of locking fingers initially spreads the locking fingers apart and when the peak and furrow are fully together a land on each locking finger positioned normal to the inward taper of the ramp of each and engages with the shoulder securing the knob in the groove.

4. An adapter and cap assembly comprising:

a housing with a input and an output, the housing having a passage aligned along an axis of the housing and passing from the input to the output, the housing having a generally cylindrical inlet extending from the housing in a first direction normal relative to the axis, the inlet having an intersection with the housing for permitting fluid communication between the inlet and the passage, the inlet having a mouth shaped therewithin for connecting in fluid tight manner with an infusion device, the mouth having lips extending radially therefrom;

a cap having a generally cylindrical side wall with an inner surface configured to conjugate with and close the inlet when placed thereover and to open the mouth when the cap is removed therefrom, an undercut in the inner side wall of the cap to conjugate and releasably lock to the lips, a protrusion extends from the side wall one way and a living hinge terminating in a knob extends the other way, the protrusion can be used to remove the cap from the inlet when the undercut thereon is engaged with the lips; and a pair of opposed locking fingers extends from the housing defining a groove therebetween, the locking fingers shaped for receiving and securing therebetween the knob in the groove, the knob has a camming nose with opposed tapers which cooperate with a ramp on each of the pair of locking fingers to spread the fingers as the knob is inserted therebetween to ease the seating of the knob in the groove, the knob has a distal end with a furrow located transverse thereto and the groove has a peak transversely centered therein so that the central position of the knob in the groove is maintained upon engagement, the knob is transversely thicker than the living hinge and the knob extends normal thereto with a shoulder thereabout, each ramp has an opposed central recess for cooperating as the camming nose is forced thereover and between so that the conjugating motion of the knob and the pair of locking fingers spreads the locking fingers apart until the peak and furrow are fully together, on each locking finger a land positioned normal to the inward taper of the ramp of each and located above the groove engages the shoulder on the knob.

5. The method of claim 4 with the added step of directing with a central recess in each ramp that cooperates with the tapers as the camming nose is forced thereover and between so that the conjugating step for the knob and the pair of locking fingers guides the knob into the center of the groove.

6. A method for assembling an adapter with an inlet cap including the following steps:

assembling an adapter to a cap, the adapter comprising a housing with an input and an output, the housing having a passage aligned along an axis thereof between the input and output, the housing having an inlet extending from the housing, the inlet having an intersection for permitting fluid communication with the passage and having a pair of opposed locking fingers extending from the housing with a groove therebetween for receiving and securing a knob, and the cap comprising a living hinge including a knob having a camming nose with opposed tapers and a shoulder at a transversely thicker portion where the knob is joined to the living hinge;

holding the cap by the living hinge, the cap further having a side wall with an inner surface configured to conjugate with and close the inlet when placed thereover, the living hinge of the cap extending from and terminating in the knob;

placing the knob, above the locking fingers which have a ramp on each so that the cap will conjugate with the inlet;

spreading the fingers by inserting the camming nose between the ramps to move the locking fingers apart to ease the seating of the knob in the groove as the knob is pressed toward the housing in a direction normal to the axis; and centering the knob in the groove with a furrow located transversely across a distal end of the knob and with a peak centered in and transversely across the groove.

* * * * *